United States Patent [19]

Okamoto

[11] Patent Number: 5,550,016
[45] Date of Patent: Aug. 27, 1996

[54] OLIGONUCLEOTIDES OF HCV, PRIMERS AND PROBES THEREFROM, METHOD OF DETERMINING HCV GENOTYPES AND METHOD OF DETECTING HCV IN SAMPLES

[75] Inventor: Hiroaki Okamoto, Tochigi, Japan

[73] Assignee: Immuno Japan Inc., Tokyo, Japan

[21] Appl. No.: 157,235

[22] Filed: Nov. 24, 1993

[30] Foreign Application Priority Data

Nov. 27, 1992 [JP] Japan ..................................... 4-354370

[51] Int. Cl.$^6$ .............................. C12Q 1/70; C12Q 1/68; C07H 21/04; C12N 15/00
[52] U.S. Cl. .................................. 435/5; 435/6; 435/91.1; 435/91.2; 536/24.32; 536/24.33; 536/25.3; 935/76; 935/77; 935/78
[58] Field of Search .................................. 435/5, 6, 91.1, 435/91.2; 536/24.32, 24.33, 25.3; 935/76–78

[56] References Cited

U.S. PATENT DOCUMENTS 5,350,671  9/1994  Houghton et al. ........................... 435/5
5,427,909  6/1995  Okamoto et al. .......................... 435/54

*Primary Examiner*—W. Gary Jones
*Assistant Examiner*—Bradley L. Sisson
*Attorney, Agent, or Firm*—Beveridge, DeGrandi, Weilacher & Young, L.L.P.

[57] ABSTRACT

Disclosed are nucleotide sequences of the 5' noncoding region and the following structural protein coding region of HCV which have not been previously discovered, and a method to detect HCV with high specificity and good sensitivity using the oligonucleotides as a primer or a probe in order to detect extensively HCV genes of more varied strains.

19 Claims, No Drawings

OLIGONUCLEOTIDES OF HCV, PRIMERS AND PROBES THEREFROM, METHOD OF DETERMINING HCV GENOTYPES AND METHOD OF DETECTING HCV IN SAMPLES

BACKGROUND AND INTRODUCTION

The present invention concerns partial genetic nucleotides of hepatitis C virus (hereinafter "HCV"), specific primers and probes, and method of determining HCV genotypes and method of detecting HCV in samples utilizing such primers and probes.

After the presentation of the partial sequence of genomic nucleotides of HCV in 1988 by the researchers of Chiron Corp., diagnostic systems were developed to detect HCV antibodies using recombinant proteins and synthetic peptides based on the nucleotide sequences. These techniques are today put to practical use in the screening of bloods for transfusion and in the diagnosis of patients. The antibody test, however, can not completely detect HCV carriers. In addition, it is not sensitive enough to judge the patients' condition in either acute or chronic hepatitis, for establishment of guidance of treatment, and for judging the effect of treatment.

As a result, besides the antibody test, diagnostic methods to detect HCV carriers were researched and developed in order to detect HCV genes with high specificity and good sensitivity. Because of the high variability of HCV, these detection systems were developed with the intention to detect conservative regions of HCV genes by comparing those sequences of HCV strains available to the public today. Though those detection methods using nucleotides really provide more useful information than methods using antibodies, there are still some cases of HCV carriers reported where there was no detection of HCV gene, thus indicating that the detection systems still do not have satisfactory performance.

Accordingly, there is desired the establishment of an improved method to detect HCV genes which covers more HCV strains.

SUMMARY OF THE INVENTION

An object of the present invention is to reveal new nucleotide sequences of the 5' noncoding region and the following structural protein coding region of HCV which have not been previously discovered, to obtain oligonucleotides of a part of the new sequences, to provide a method to detect HCV with high specificity and good sensitivity using the oligonucleotides as a primer or a probe in order to detect extensively HCV genes of more varied strains, and to provide a method to determine the HCV genotype using the oligonucleotides as a primer or a probe.

DETAILED DESCRIPTION OF THE INVENTION

The oligonucleotides, primers and probes, and methods of the present invention can be utilized in screening of bloods; determining differences in response to treatments by types I-VI of HCV; and in epidemiology in tracing the source of HCV infection.

Disclosed are new nucleotide sequences of HCV nonstructural protein region 5 from sera containing sufficient amounts of HCV-RNA tested by Polymerase Chain Reaction (hereinafter "PCR") using primers based on the 5' noncoding region previously reported (Japan. J. Exp. Med. (1990), volume 60, pages 167–177), which failed to be identified by genotypes using the method previously reported (J. Gen. Virol. (1992), volume 73, pages 673–679) using primers based on the core region of HCV.

As a result, HCV-RNAs obtained from the sera were found not to be type I to IV, but to have high homology to genotypes tentatively called V and VI.

Nucleotides having 803 base pairs (45th to 847th) from the 5' terminus of the cDNA of HCV-RNAs, which are assumed to be the 5' noncoding region and a part of following structural protein, were determined and found to be very conservative.

In addition, some of the regions which were previously considered conservative in HCV strains, and optimal to use as the sequences as primers for detection of HCV, were found to have some varieties in the new strains.

On the basis of those nucleotides found, the inventor found a new region which could be utilized as a primer or a probe with high specificity and good sensitivity in HCV-RNA in common with not only types I to IV but V and VI to complete the invention.

The present invention concerns polynucleotides and oligonucleotides which are all of or parts of the 5' noncoding region and/or the following structural protein region, especially the nucleotides having the sequences of all or parts of the SEQ ID Nos. 1 to 7 and those having complementary sequence to the nucleotides.

The present invention also concerns primers, probes and labeled probes having the sequence of nucleotides described herein, and a method to detect HCV using those primers and probes, especially using primers having nucleotides sequences of SEQ ID NOS. 7 to 10.

SEQ ID NOS. 1 to 6 respectively show (+) strain sequence of 803 nucleotides (45th to 847th) from the 5' terminus of strains Mit/92, Hir/92, Th-85, NZL-1, US-114 and Th-103.

SEQ ID NOS. 7-10 respectively show sequences of oligonucleotides which can be used as primers or probes, whose nucleotide number from the 5' terminus of HCV-RNA is described below.

Disclosed are nucleotide sequences of the 5' noncoding region and the following upstream parts of the region coding for structural protein. The comparison of the results with the same regions of sequences of HCV strains I to IV previously found by the inventor showed the regions also conservative in the new strains.

On the basis of the oligonucleotides found, the inventor found an oligonucleotide which can be used as a primer or a probe to detect HCV not only of types I to IV but V and VI. The inventor also found the method to detect HCV independently from the genotypes of HCV strains with high specificity and good sensitivity using the oligonucleotides.

Since polynucleotides and oligonucleotides of the present invention are characterized as consisting of the 5' noncoding region and the following region coding for a part of structural protein, the present invention also includes the nucleotides having some substitutions originating in differences between strains.

According to the present invention, pairs of oligonucleotides can be used as primers in order to detect HCV by the amplification of complementary DNA (cDNA) in which PCR can be used preferably.

The preferred procedure for the detection of HCV-RNA according to the present invention is the amplification of HCV cDNA by first stage PCR followed by second stage PCR using the amplification product of the first. The primer pair used in the second stage amplification should be annealed inside of the first stage pair.

Polynucleotides and oligonucleotides of the present invention are specific to all or parts of the genomic nucleotides of the 5' noncoding region and the following upstream parts of the region coding for structural protein of HCV-RNA. The oligonucleotides selected from those nucleotides can be used as primers or probes.

The good primers used in the method of the present invention to detect HCV are #299 (nts. 250–269), #32a (nts. 45–64), #33 (nts. 63–82), and #48 (nts. 188–207), which sequences are showed respectively in SEQ ID NOS. 7 to 10. Nts. shows nucleotide number from the 5' terminus when assumed the sequence to that of HC-J1.

The nucleotides of the present invention can be obtained by chemical synthesis and used for the detection of HCV by other than PCR. For instance, the nucleotides can be used as probes, and the probes work more effectively when used after being labeled with enzyme, radioisotope, luminescent substance, and other substances known in the art.

Table 1 shows the comparison of nucleotide sequences of 337 bp in the NS5 region obtained from the samples with strains previously available to the public. For example, Mit/92 displays 65.1% homology with HCV-1 (Genotype I) but displays 97.3% homology with T-1 (Genotype V).

Table 2 shows the result of the HCV related markers among blood donors testing positive for HCV-RNA.

Table 3 shows nucleotide sequences in the HCV strains types I to VI of the region corresponding to primer #36 (SEQ ID NO: 14) (nts. 246–269) which can be used as a primer or a probe in detection of HCV types I to IV. The nucleotides of the sequences are indicated in (+) strand.

Table 4 shows nucleotide sequences in the HCV strains types I to VI of the region corresponding to primer #299 (SEQ ID NO: 18) (nts. 250–269) which can be used as a primer or a probe in detection of HCV types I to VI. The nucleotides of the sequences are indicated in (+) strand.

The method of the present invention provides detection of HCV with high specificity and good sensitivity; also provided are primers and probes to be used in the method. The present invention also provides polynucleotides and oligonucleotides from which primers and probes of the invention can be obtained.

It will also be understood that the practice of the present invention is not limited to the use of the exact sequence of SEQ ID NOS. 1–10. Modifications to the sequence, such as deletions, insertions, or substitutions in the sequence are also contemplated. For example, alteration in the gene sequence which reflect the degeneracy of the genetic code are contemplated. Therefore, where the phrase SEQ ID NOS. 1–10 is used in either the specification or the claims, it will be understood to encompass all such modifications and variations. In particular, the invention contemplates those nucleic acid sequences which are sufficiently duplicative of SEQ ID NOS. 1–10 so as to permit hybridization therewith under standard high stringency southern hybridization conditions, such as those described in Maniatis et al. (Molecular Cloning. A Laboratory Manual, 2nd ed. Cold Spring Harbor Laboratory, 1989).

Samples from patients, in which the presence of HCV is to be determined, may be for example blood, serum, and other body fluids or tissues.

Examples of applications of the present invention are shown below; however, the invention shall in no way be limited to those examples.

EXAMPLES

Example 1

The genotypes and nucleotide sequences of the 5' noncoding region of HCV-RNA obtained from sera having enough HCV-RNA (but in which it was impossible to determine genotypes using the previously developed method) were determined in the following way:

(1) Isolation of RNA

RNA from serum samples, Mit/92, Hir/92, Th-85, NZI-1, US-114 and Th-103, which were confirmed to have enough HCV-RNA using the conventional method by amplification of the 5' noncoding region (but in which it was impossible to determine genotypes based on core region sequence previously developed by the inventor) were isolated in the following method.

50 µl of each serum sample were added to Tris-chloride buffer (10mM, ph 8.0) and centrifuged at 90×10$^3$ rpm for 15 minutes. The precipitate was suspended in Tris-chloride buffer (50 mM, pH 8.0, containing 200 mM NaCl, 10 mM EDTA, 2% (w/v) sodium dodecyl sulfate (SDS) and proteinase K 1 mg/ml), and incubated at 60° C. for 1 hour. Then the nucleic acids were extracted by phenol/chloroform and precipitated by ethanol to obtain RNAs.

(2) Synthesis of cDNA

The isolated RNA were heated at 70° C. for 1 minute; using this as a template, cDNA was synthesized by reacting at 42° C. for 1 hour using 20 pmol of oligonucleotide primer #81 (SEQ ID NO: 11) (5'-GACACCCCGCT-GTTTTGACTC-3'; nt 8613–8632 from the 5' terminus) and 100 units of reverse transcriptase (Superscript, GIBCO-BRL)

(3) Amplification of NS5 region cDNA by PCR

Using the cDNA as a template, 377 bp nucleotide from nt 8256 to 8632 in the NS5 region was amplified using NS5 specific primers #80 (SEQ ID NO: 12) (5'-GACACCCGCT-GTTTTGA CTC-3'; nt 8256–8275) as a sense primer and #81 as an antisense primer. cDNA was amplified for 35 cycles using Gene Amp DNA Amplification Reagent (Perkin Elmer Cetus) on a DNA Thermal Cycler (Perkin-Elmer Cetus). PCR was carried out by the following reaction cycle: denaturation at 94° C. for 1 minute, annealing of primers at 55° C. for 1.5 minutes, and extension at 72° C. for 2 minutes.

(4) Determination of Nucleotide Sequence of NS5 Region

Nucleotides of the NS5 region was amplified by PCR followed by treatment using T4 Polynucleotide Kinase (New England Biolabs) and T4 DNA Polymerase (Takara Biochemicals). Then the fragment was inserted into M13 phage vector and cloned. Determination of the sequence was carried out by dideoxy chain termination method using Sequenase sequencing kit ver. 2.0 (United States Biochemicals) and AutoRead Sequencing kit (Pharmacia-LKB).

Table 1 shows homology (%) of 337 bp nucleotide sequences (excluding primers) in the NS5 region obtained from 6 samples against 6 genotypes. As result Mit/92, Hir/92, Th-85, NZL-1 and US-114 showed high homology with a type tentatively called type V, whereas Th-103 showed high homology with a type tentatively called type VI.

Example 2

Nucleotide sequences of the 5' noncoding region and the following structural protein region of HCV strains which were classified as types tentatively called types V and VI.
(1 ) Determination of sequence According to the method shown in Example 1, HCV-RNA was extracted and cDNA from the RNA was synthesized. cDNA synthesis was carried out using primer #122 (SEQ ID NO: 13) (5'-AGGTTCCCTGTTGCATAGTT-3', nt 828–347) specific to the structural protein region. Then nucleotides of the 5' noncoding region and the structural protein region was amplified by PCR in the same way as in Example 1 using primer pair #32a and #122, but extension time was changed to 3 minutes.

The 803 nucleotides obtained were cloned into M13 phage vector, then the sequence determined in the same way as in Example 1.

SEQ ID NOS. 1 to 6 show the sequences of the determined region.

Example 3

Designation of primer useful for detection of genomic RNA of HCV tentatively called types V and VI.

From the study of the 5' noncoding region and the following structural protein region of the new sequences obtained in Example 2, specific nucleotide sequences which show high homology not only among I to IV but V and VI was searched, and a new primer useful for detection of genomic RNA of HCV of any genotype strain was designed.

Since the region is conservative, oligonucleotide primers developed previously by the inventor in order to detect HCV were examined in order to determine whether they could be utilized for the purpose of the invention. Primers #32a, #33, #48 and #36 were used to detect HCV-RNA in the conventional method previously developed (Japan J. Exp. Med., (1990), volume 60, pages 167–177). Since primer #32a (SEQ ID NO. 8), used in the first PCR as sense primer, showed its effect in amplification in Example 2, it was confirmed to be sufficiently used in the invention. Since primer #33 (SEQ ID NO. 9), used in the second PCR as the sense primer, had only 2 central substitution in 20 bases, the specificity as the primer was judged to remain. As for primer #48 (SEQ ID NO. 10), used in the second PCR as the antisense primer, two substitutions were found in fourth and fifth positions from the 5' end, which specificity as a primer was judge to remain. Since primer #36, used in the first PCR as the antisense primer, however, had three successive substitutions found from the third to fifth positions from 5' end, its specificity as a primer was expected to be less than the other three. On this basis there was found a sequence which could be used as the primer for the detection not only of types I to IV, but types V and VI near #36. As a result, primer #299 (5'-ACCCAACACTACTCGGCTAG-3', SEQ ID NO. 7) was found. This sequence corresponds to nt 250 to 269 from the 5' terminus. Though the primer had 1 or 2 substitutions compared with types V and VI, they would not be expected to reduce the specificity.

Example 4

Comparison of sensitivity in detection of HCV gene using primers #36 and #299.

From serum samples which were classified as being genotype II and confirmed to contain 107 infectious doses of HCV-RNA, HCV-RNA was detected using the conventional method utilizing primer #36 and also using the same method but utilizing primer #299 instead of primer #36. The samples were diluted and tested in order to compare the sensitivities of the two methods. In both methods RNA was detected after dilution ($\times 10^7$).

Serum sample NZL-1, found to be type V, was tested in the same way. HCV-RNA was detected after dilution at $\times 10^4$ but not after $\times 10^5$ using primer #36; HCV-RNA was detected after dilution at $\times 10^5$ using primer #299.

In addition, since the serum samples used contained more than $10^4$ infectious doses of HCV-RNA in 50 µl, RNA could be detected in the method utilizing primer #36.

Example 5

Detection of HCV-RNA from blood donors.

HCV-RNA using primer #299 from serum samples of 3383 normal Japanese blood donors whose sera tested positive by the second generation HCV antibody test (PHA, Dainabot) or by HCV core antibody (O.D. of one or both of anti-CP-10 or anti-CP-9 over 1.0) or ALT≧36 Karmen Units. HCV-RNA was detected in 21 samples (0.6%). In the 21 samples, 19 were positive for PHA, 19 were positive for core antibody, and 17 positive for both. ALT was over 36 Karmen Units in 5 samples. Table 2 shows the results.

The present invention thus concerns, but is not limited to, the following:

A recombinant oligonucleotide selected from the following group:

(a) Mit/92 having the nucleotide sequence of SEQ ID NO. 1;

(b) Hir/92 having the nucleotide sequence of SEQ ID NO. 2;

(c) Th-85 having the nucleotide sequence of SEQ ID NO. 3;

(d) NZL-1 having the nucleotide sequence of SEQ ID NO. 4;

(e) US-114 having the nucleotide sequence of SEQ ID NO. 5;

(f) Th-103 having the nucleotide sequence of SEQ ID NO. 6; and (g) #299 having the nucleotide sequence of SEQ ID NO. 7.

A recombinant oligonucleotide primer or probe from the nucleotide sequence described above.

Primer #299 having the nucleotide sequence of SEQ ID NO. 7.

A method of determining the HCV genotype of a HCV strain (e.g., from a sample). The method involves subjecting the HCV strain to two stage PCR, wherein the first stage PCR involves utilizing primers #32a (SEQ ID NO. 8) and #299 (SEQ ID NO. 7) for first stage amplification and wherein the second stage PCR involves utilizing primers #33 (SEQ ID NO. 9) and #48 (SEQ ID NO. 10) for the second stage amplification. The method also involves comparing the product of the second stage PCR with HCV genotypes I, II, III, IV, V and VI. The method further involves synthesizing cDNA from viral RNA of the HCV strain.

A method of determining the HCV genotype of a HCV strain (e.g., from a sample). The method involves subjecting the HCV strain to PCR, wherein primer #32a (SEQ ID NO. 8) or primer #33 (SEQ ID NO. 9) is utilized as a sense primer and primer #299 (SEQ ID NO. 7) or primer #48 (SEQ ID NO. 10) is utilized as an antisense primer. The method further involves comparing the product of said second stage PCR with HCV genotypes I, II, III, IV, V and VI. The method further involves synthesizing cDNA from viral RNA of the HCV strain.

A test kit for diagnosing HCV or for detecting HCV, the kit containing at least one primer described above. The test kit can also contain (a) dATP, dTTP, dGTP, and dCTP; and (b) heat stable DNA polymerase.

A method for detecting HCV in a sample. The method involves subjecting the sample to two stage PCR, wherein the first stage PCR involves utilizing primers #32a (SEQ ID NO. 8) and #299 (SEQ ID NO. 7) for first stage amplification and wherein the second stage PCR involves utilizing primers #33 (SEQ ID NO. 9) and #48 (SEQ ID NO. 10) for the second stage amplification. The method further involves obtaining a sample from a patient. The method further involves synthesizing cDNA from viral RNA from the sample.

A method for detecting HCV in a sample. The method involves subjecting the sample to PCR, wherein primer #32a (SEQ ID NO. 8) or primer #33 (SEQ ID NO. 9) is utilized as a sense primer and primer #299 (SEQ ID NO. 7) or primer #48 (SEQ ID NO. 10) is utilized as an antisense primer. The method further involves obtaining a sample from a patient. The method further involves synthesizing cDNA from viral RNA from the sample.

Japanese Priority Application 354370/92 filed on Nov. 27, 1992 is relied on and incorporated by reference.

Japanese Patent Application No. 196175/91 and U.S. patent application Ser. No. 07/866,045 (filed on Apr. 9, 1992); Japanese Patent Application Nos. 287402/91 and 360441/91, and U.S. patent application Ser. No. 07/925,695 (filed on Aug. 7, 1992); Japanese Patent Application Nos. 307296/91, 93960/92, and 276502/92), and U.S. patent application Ser. No. 07/940,242 (filed on Sep. 8, 1992); and Japanese Patent Application No. 361488/91 and U.S. Patent Application Ser. No. 07/995,171 (filed on Dec. 24, 1992) are incorporated by reference.

Japan. J. Exp. Med. (1990), volume 60, pages 167–177, and J. Gen. Virol. (1992), volume 73, pages 673–679 are incorporated by reference.

What is claimed:

1. A recombinant oligonucleotide selected from the group consisting of:

(a) Mit/92 having the nucleotide sequence of SEQ ID NO. 1;

(b) Hir/92 having the nucleotide sequence of SEQ ID NO. 2;

(c) Th-85 having the nucleotide sequence of SEQ ID NO. 3;

(d) NZL-1 having the nucleotide sequence of SEQ ID NO. 4;

(e) US-114 having the nucleotide sequence of SEQ ID NO. 5;

(f) Th-103 having the nucleotide sequence of SEQ ID NO. 6; and (g) #299 having the nucleotide sequence of SEQ ID NO. 7.

2. A recombinant oligonucleotide primer or probe from the nucleotide sequence according to claim 1 wherein said oligonucleotide primer or probe specifically hybridizes with HCV genotypes, I, II, III, IV, V, and VI.

3. The oligonucleotide primer according to claim 2, said primer is oligonucleotide primer #299 (SEQ ID NO. 7).

4. A method of determining the HCV genotype of a HCV strain, said method comprising subjecting said HCV strain to two stage PCR, wherein the first stage PCR comprises utilizing primers #32a (SEQ ID NO. 8) and #299 (SEQ ID NO. 7) for first stage amplification and wherein the second stage PCR comprises utilizing primers #33 (SEQ ID NO. 9) and #48 (SEQ ID NO. 10) for the second stage amplification; said method further comprising comparing the product of said second stage PCR with HCV genotypes I, II, III, IV, V and VI.

5. The method according to claim 4, further comprising synthesizing cDNA from viral RNA of said HCV strain.

6. A method of determining the HCV genotype of a HCV strain, said method comprising subjecting said HCV strain to PCR, wherein primer #32a (SEQ ID NO. 8) or primer #33 (SEQ ID NO. 9) is utilized as a sense primer and primer #299 (SEQ ID NO. 7) or primer #48 (SEQ ID NO. 10) is utilized as an antisense primer; said method further comprising comparing the product of said second stage PCR with HCV genotypes I, II, III, IV, V and VI.

7. The method according to claim 6, further comprising synthesizing cDNA from viral RNA of said HCV strain.

8. A test kit for diagnosing HCV or for detecting HCV, said kit comprising at least one primer according to claim 2.

9. The test kit according to claim 8, further comprising (a) dATP, dTTP, dGTP, and dCTP; and (b) heat stable DNA polymerase.

10. A method for detecting HCV in a sample, said method comprising subjecting said sample to two stage PCR, wherein the first stage PCR comprises utilizing primers #32a (SEQ ID NO. 8) and #299 (SEQ ID NO. 7) for first stage amplification and wherein the second stage PCR comprises utilizing primers #33 (SEQ ID NO. 9) and #48 (SEQ ID NO. 10) for the second stage amplification, and detecting the product of said second stage amplification.

11. The method according to claim 10, further comprising obtaining a sample from a patient.

12. The method according to claim 10, further comprising synthesizing cDNA from viral RNA from said sample.

13. A method for detecting HCV in a sample, said method comprising subjecting said sample to PCR, wherein primer #32a (SEQ ID NO. 8) or primer #33 (SEQ ID NO. 9) is utilized as a sense primer and primer #299 (SEQ ID NO. 7) or primer #48 (SEQ ID NO. 10) is utilized as an antisense primer, and detecting the product of said PCR.

14. The method according to claim 13, further comprising obtaining a sample from a patient.

15. The method according to claim 13, further comprising synthesizing cDNA from viral RNA from said sample.

16. The method according to claim 10, wherein said HCV is a member of HCV genotypes I, II, III, IV, V or VI.

17. The method according to claim 13, wherein said HCV is a member of HCV genotypes I, II, III, IV, V or VI.

18. A method of determining the HCV genotype of a HCV strain in a sample, said method comprising subjecting said sample to two stage PCR, wherein the first stage PCR comprises utilizing primers #32a (SEQ ID NO. 8) and #299 (SEQ ID NO. 7) for first stage amplification and wherein the second stage PCR comprises utilizing primers #33 (SEQ ID NO. 9) and #48 (SEQ ID NO. 10) for the second stage amplification; said method further comprising comparing the product of said second stage PCR with HCV genotypes I, II, III, IV, V and VI.

19. A method of determining the HCV genotype of a HCV strain in a sample, said method comprising subjecting said sample to PCR, wherein primer #32a (SEQ ID NO. 8) or primer #33 (SEQ ID NO. 9) is utilized as a sense primer and primer #299 (SEQ ID NO. 7) or primer #48 (SEQ ID NO. 10) is utilized as an antisense primer; said method further comprising comparing the product of said second stage PCR with HCV genotypes I, II, III, IV, V and VI.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 803 base pairs
( B ) TYPE: nucleic acid
( C ) STRANDEDNESS: single
( D ) TOPOLOGY: linear ( x i ) SEQUENCE DESCRIPTION: SEQ ID NO:1:

```
CTGTGAGGAA  CTACTGTCTT  CACGCGGAAA  GCGCCTAGCC  ATGGCGTTAG  TACGAGTGTC   60
GTGCAGCCTC  CAGGACCCCC  CCTCCCGGGA  GAGCCATAGT  GGTCTGCGGA  ACCGGTGAGT  120
ACACCGGAAT  CGCTGGGGTG  ACCGGGTCCT  TTCTTGGAGC  AACCCGCTCA  ATACCCAGAA  180
ATTTGGGCGT  GCCCCCGCAA  GATCACTAGC  CGAGTAGTGT  TGGGTCGCGA  AAGGCCTTGT  240
GGTACTGCCT  GATAGGGTGC  TTGCGAGTGC  CCCGGGAGGT  CTCGTAGACC  GTGCAACATG  300
AGCACACTTC  CTAAACCTCA  AAGAAAAACC  AAAAGAAACA  CCATCCGTCG  CCCACAGGAC  360
ATCAAGTTCC  CGGGTGGCGG  ACAGATCGTT  GGTGGAGTAT  ACGTGTTGCC  GCGCAGGGGC  420
CCACGATTGG  GTGTGCGCGC  GACGCGTAAA  ACTTCTGAAC  GGTCACAGCC  TCGCGGACGA  480
CGACAGCCTA  TCCCCAAGGC  GCGTCGGAGC  GAAGGCCGGT  CCTGGGCTCA  GCCCGGGTAC  540
CCTTGGCCCC  TCTATGGTAA  CGAGGGCTGC  GGGTGGGCAG  GGTGGCTCCT  GTCCCCACGC  600
GGCTCCCGTC  CAACTTGGGG  CCCAAACGAC  CCCCGGCGGA  GGTCCCGCAA  TTTGGGTAAA  660
GTCATCGATA  CCCTTACGTG  CGGTTTCGCC  GACCTCATGG  GGTACATCCC  GCTCGTCGGC  720
GCTCCCGTAG  GAGGCGTCGC  AAGAGCCCTC  GCGCATGGCG  TGAGGGCCCT  TGAAGACGGG  780
ATTAATTATG  CAACAGGGAA  CCT                                            803
```

( 2 ) INFORMATION FOR SEQ ID NO:2:

( i ) SEQUENCE CHARACTERISTICS:
( A ) LENGTH: 803 base pairs
( B ) TYPE: nucleic acid
( C ) STRANDEDNESS: single
( D ) TOPOLOGY: linear ( x i ) SEQUENCE DESCRIPTION: SEQ ID NO:2:

```
CTGTGAGGAA   CTACTGTCTT   CACGCGGAAA   GCGCCTAGCC   ATGGCGTTAG   TACGAGTGTC        60

GTGCAGCCTC   CAGGACCCCC   CCTCCCGGGA   GAGCCATAGT   GGTCTGCGGA   ACCGGTGAGT       120

ACACCGGAAT   CGCTGGGGTG   ACCGGTCCT    TTCTTGGAGT   AACCCGCTCA   ATACCCAGAA       180

ATTTGGGCGT   GCCCCCGCGA   GATCACTAGC   CGAGTAGTGT   TGGGTCGCGA   AAGGCCTTGT       240

GGTACTGCCT   GATAGGGTGC   TTGCGAGTGC   CCCGGGAGGT   CTCGTAGACC   GTGCAACATG       300

AGCACACTTC   CTAAACCTCA   AAGAAAAACC   AAAAGAAACA   CCATCCGTCG   CCCACAGGAC       360

GTCAAGTTCC   CGGGTGGCGG   ACAGATCGTT   GGTGGAGTAT   ACGTGTTGCC   GCGCAGGGGC       420

CCACGATTGG   GTGTGCGCGC   AACGCGTAAA   ACTTCTGAAC   GGTCGCAGCC   TCGTGGACGA       480

CGACAGCCTA   TCCCCAAGGC   GCGTCGGAAC   GAAGGCCGGT   CCTGGGCTCA   GCCCGGGTAC       540

CCTTGGCCCC   TCTATGGTAA   CGAGGGCTGC   GGGTGGGCAG   GGTGGCTCCT   GTCCCACGT        600

GGCTCCCGTC   CATCTTGGGG   CTCAAACGAC   CCCCGGCGGA   GGTCCCGCAA   TTTGGGTAAA       660

GTCATCGATA   CCCTTACGTG   CGGATTCGCC   GACCTCATGG   GGTACATCCC   GCTCGTCGGC       720

GCTCCCGTAG   GGGGCGTCGC   AAGACCCCTC   GCGCATGGCG   TGAGGGCCCT   TGAAGACGGG       780

ATAAATTATG   CAACAGGGAA   CCT                                                    803
```

( 2 ) INFORMATION FOR SEQ ID NO:3:

( i ) SEQUENCE CHARACTERISTICS:
        ( A ) LENGTH: 803 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CTGTGAGGAA   CTACTGTCTT   CACGCGGAAA   GCGCCTAGCC   ATGGCGTTAG   TACGAGTGTC        60

GTGCAGCCTC   CAGGACCCCC   CCTCCCGGGA   GAGCCATAGT   GGTCTGCGGA   ACCGGTGAGT       120

ACACCGGAAT   CGCTGGGGTG   ACCGGTCCT    TTCTTGGAAC   AACCCGCTCA   ATACCCAGAA       180

ATTTGGGCGT   GCCCCCGCGA   GATCACTAGC   CGAGTAGTGT   TGGGTCGCGA   AAGGCCTTGT       240

GGTACTGCCT   GATAGGGTGC   TTGCGAGTGC   CCCGGGAGGT   CTCGTAGACC   GTGCAACATG       300

AGCACACTTC   CTAAACCTCA   AAGAAAAACC   AAAAGAAACA   CCATCCGTCG   CCCACAGGAC       360

GTTAAGTTCC   CGGGTGGCGG   ACAGATCGTT   GGTGGAGTAT   ACGTGTTGCC   GCGCAGGGGC       420

CCAAGATTGG   GTGTGCGCGC   GACGCGTAAA   ACTTCTGAAC   GGTCACAGCC   TCGCGGACGA       480

CGACAGCCTA   TCCCCAAGGC   ACGTCGGAGC   GAAGGCCGGT   CCTGGGCTCA   GCCTGGGTAC       540

CCTTGGCCCC   TCTATGGTAA   CGAGGGCTGC   GGGTGGGCAG   GGTGGCTCCT   GTCCCACGC        600

GGCTCCCGTC   CATCTTGGGG   CCCAAACGAC   CCCCGGCGAC   GGTCCCGCAA   TTTGGGTAAA       660

GTCATCGATA   CCCTTACGTG   CGGATTCGCC   GACCTCATGG   GGTACATCCC   GCTCGTCGGC       720

GCTCCCGTAG   GAGGCGTCGC   AAGAGCCCTC   GCGCATGGCG   TGAGGGCCCT   TGAAGACGGG       780

ATAAATTATG   CAACAGGGAA   CCT                                                    803
```

( 2 ) INFORMATION FOR SEQ ID NO:4:

( i ) SEQUENCE CHARACTERISTICS:
        ( A ) LENGTH: 803 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
CTGTGAGGAA   CTACTGTCTT   CACGCGGAAA   GCGTCTAGCC   ATGGCGTTAG   TACGAGTGTC        60
```

| GTGCAGCCTC | CAGGACCCCC | CCTCCCGGGA | GAGCCATAGT | GGTCTGCGGA | ACCGGTGAGT | 120 |
| ACACCGGAAT | CGCTGGGGTG | ACCGGGTCCT | TTCTTGGAGC | AACCCGCTCA | ATACCCAGAA | 180 |
| ATTTGGGCGT | GCCCCCGCGA | GATCACTAGC | CGAGTAGTGT | TGGGTCGCGA | AAGGCCTTGT | 240 |
| GGTACTGCCT | GATAGGGTGC | TTGCGAGTGC | CCCGGGAGGT | CTCGTAGACC | GTGCAACATG | 300 |
| AGCACACTTC | CTAAACCTCA | AGAAAAACC | AAAAGAAACA | CCATCCGTCG | CCCACAGGAC | 360 |
| GTCAAGTTCC | CGGGTGGCGG | ACAGATCGTT | GGTGGAGTAT | ACGTGTTGCC | GCGCAGGGGC | 420 |
| CCACGATTGG | GTGTGCGCGC | GACGCGTAAA | ACTTCTGAAC | GGTCACAGCC | TCGCGGACGA | 480 |
| CGACAGCCTA | TCCCCAAGGC | GCGTCGGAGC | GAAGGCCGGT | CCTGGGCTCA | GCCCGGGTAC | 540 |
| CCTTGGCCCC | TCTATGGTAA | CGAGGGCTGC | GGGTGGGCAG | GGTGGCTCCT | GTCCCACGC | 600 |
| GGCTCCCGTC | CATCCTGGGG | CCCAAATGAC | CCCCGGCGGA | GGTCCCGCAA | TTTGGGTAAA | 660 |
| GTCATCGATA | CCCTAACGTG | CGGATTCGCC | GACCTCATGG | GGTACATCCC | GCTCGTCGGC | 720 |
| GCTCCTGTAG | GAGGCGTCGC | AAGAGCCCTC | GCGCATGGCG | TGAGGGCCCT | TGAAGACGGG | 780 |
| ATAAATTATG | CAACAGGGAA | CCT | | | | 803 |

(2) INFORMATION FOR SEQ ID NO:5:

(i) SEQUENCE CHARACTERISTICS:
        (A) LENGTH: 803 base pairs
        (B) TYPE: nucleic acid
        (C) STRANDEDNESS: single
        (D) TOPOLOGY: linear (xi) SEQUENCE DESCRIPTION: SEQ ID NO:5:

| CTGTGAGGAA | CTACTGTCTT | CACGCGGAAA | GCGTCTAGCC | ATGGCGTTAG | TACGAGTGTC | 60 |
| GTGCAGCCTC | CAGGACCCCC | CCTCCCGGGA | GAGCCATAGT | GGTCTGCGGA | ACCGGTGAGT | 120 |
| ACACCGGAAT | CGCTGGGGTG | ACCGGGTCCT | TTCTTGGAGC | AACCCGCTCA | ATACCCAGAA | 180 |
| ATTTGGGCGT | GCCCCCGCGA | GATCACTAGC | CGAGTAGTGT | TGGGTCGCGA | AAGGCCTTGT | 240 |
| GGTACTGCCT | GATAGGGTGC | TTGCGAGTGC | CCCGGGAGGT | CTCGTAGACC | GTGCAACATG | 300 |
| AGCACACTTC | CTAAACCTCA | AGAAAAACC | AAAAGAAACA | CCATCCGTCG | CCCACAGGAC | 360 |
| GTCAAGTTCC | CGGGTGGCGG | ACAGATCGTT | GGTGGAGTAT | ACGTGTTGCC | GCGCAGGGGC | 420 |
| CCACGATTGG | GTGTGCGCGC | GACGCGTAAA | ACTTCTGAAC | GGTCACAGCC | TCGCGGACGA | 480 |
| CGACAGCCTA | TCCCCAAGGC | GCGTCGGAGC | GAAGGCCGGT | CCTGGGCTCA | GCCCGGGTAC | 540 |
| CCTTGGCCCC | TCTATGGTAA | CGAGGGCTGC | GGGTGGGCAG | GATGGCTCCT | GTCCCGCGC | 600 |
| GGCTCCCGTC | CATCATGGGG | CCCAAATGAC | CCCCGGCGGA | GGTCCCGCAA | TTTGGGTAAA | 660 |
| GTCATCGATA | CCCTTACGTG | CGGATTCGCC | GACCTCATGG | GGTACATCCC | GCTCGTCGGC | 720 |
| GCTCCCGTGG | GAGGCGTCGC | AAGAGCCCTC | GCGCATGGCG | TGAGGGCCCT | TGAAGACGGG | 780 |
| ATTAATTATG | CAACAGGGAA | CCT | | | | 803 |

(2) INFORMATION FOR SEQ ID NO:6:

(i) SEQUENCE CHARACTERISTICS:
        (A) LENGTH: 803 base pairs
        (B) TYPE: nucleic acid
        (C) STRANDEDNESS: single
        (D) TOPOLOGY: linear (xi) SEQUENCE DESCRIPTION: SEQ ID NO:6:

| CTGTGAGGAA | CTACTGTCTT | CACGCGGAAA | GCGTCTAGCC | ATGGCGTTAG | TACGAGTGTC | 60 |
| GTGCAGCCTC | CAGGCCCCCC | CCTCCCGGGA | GAGCCATAGT | GGTCTGCGGA | ACCGGTGAGT | 120 |

```
ACACCGGAAT  CGCCAGGTTG  ACCGGGTCCT  TTCTTGGAAC  AACCCGCTCA  ATGCCTGGAA      180

ATTTGGGCGT  GCCCCCGCGA  GATCACTAGC  CGAGTAGTGT  TGGGTCGCGA  AAGGCCTTGT      240

GGTACTGCCT  GATAGGGTGC  TTGCGAGTGC  CCCGGGAGGT  CTCGTAGACC  GTGCATCATG      300

AGCACACTTC  CCAAACCTCA  AAGACAAACC  AAAAGAAACA  CACCCCGTCG  CCCACAGAAC      360

GTCAAGTTCC  CGGGCGGCGG  GCAGATCGTT  GGTGGAGTAT  ATGTGCTGCC  GCGCAGGGGC      420

CCACGATTGG  GTGTGCGCGC  AGTGCGTAAG  ACTTCCGAGC  GGTCGCAACC  TCGCGGACGG      480

CGTCAGCCTA  TCCCCAAGGC  ACGCCGCGC   GAGGGCCGGT  CCTGGGCTCA  GCCTGGGTAC      540

CCTTGGCCCC  TCTACGGGAA  TGAGGGCCTT  GGGTGGGCAG  GATGGCTCCT  GTCCCCCGC      600

GGTTCTCGCC  CTAGTTGGGG  CCCAAACGAC  CCCCGGCGTA  GATCCCGCAA  TCTGGGTAAG      660

GTCATCGACA  CCCTAACGTG  CGGATTCGCC  GACCTCATGG  GGTACATTCC  GCTCATCGGC      720

GCCCCGTAG   GGGGCGTCGC  AAGAGCCCTC  GCTCATGGTG  TGAGGGCACT  TGAGGACGGA      780

GTGAATTATG  CAACAGGGAA  CCT                                                803
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
ACCCAACACT  ACTCGGCTAG                                                      20
```

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
CTGTGAGGAA  CTACTGTCTT                                                      20
```

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
TTCACGCAGA  AAGCGTCTAG                                                      20
```

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GTTGATCCAA  GAAAGGACCC                                                      20
```

( 2 ) INFORMATION FOR SEQ ID NO:11:

( i ) SEQUENCE CHARACTERISTICS:
　　　　( A ) LENGTH: 21 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:11:

GACACCCCGC TGTTTTGACT C　　　　　　　　　　　　　　　　　　　　　　　　　　21

( 2 ) INFORMATION FOR SEQ ID NO:12:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:12:

GACACCCGCT GTTTTGACTC　　　　　　　　　　　　　　　　　　　　　　　　　　20

( 2 ) INFORMATION FOR SEQ ID NO:13:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:13:

AGGTTCCCTG TTGCATAGTT　　　　　　　　　　　　　　　　　　　　　　　　　　20

( 2 ) INFORMATION FOR SEQ ID NO:14:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:14:

ACTGCTAGCC GAGTAGTGTT　　　　　　　　　　　　　　　　　　　　　　　　　　20

( 2 ) INFORMATION FOR SEQ ID NO:15:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:15:

ACTGCTAGCC GAGTAGCGTT　　　　　　　　　　　　　　　　　　　　　　　　　　20

( 2 ) INFORMATION FOR SEQ ID NO:16:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:16:

ACTGCTAGCC TAGTAGCGTT　　　　　　　　　　　　　　　　　　　　　　　　　　20

( 2 ) INFORMATION FOR SEQ ID NO:17:

( i ) SEQUENCE CHARACTERISTICS:
　　　　( A ) LENGTH: 20 base pairs (B) TYPE: nucleic acid
(C) STRANDEDNESS: single
(D) TOPOLOGY: linear (xi) SEQUENCE DESCRIPTION: SEQ ID NO:17:

ATCACTAGCC TAGTAGCGTT                                                                              20

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:18:

CTAGCCGAGT AGTGTTGGGT                                                                              20

(2) INFORMATION FOR SEQ ID NO:19:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:19:

CTAGCCGAGT AGCGTTGGGT                                                                              20

(2) INFORMATION FOR SEQ ID NO:20:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:20:

CTAGCCTAGT AGCGTTGGGT                                                                              20